(12) United States Patent
Teleki

(10) Patent No.: US 9,833,409 B2
(45) Date of Patent: Dec. 5, 2017

(54) PROCESS FOR THE PRODUCTION OF DISCRETE SOLID EXTRUDED PARTICLES

(71) Applicant: DSM IP ASSETS B. V., Heerlen (NL)

(72) Inventor: Alexandra Teleki, Heerlen (NL)

(73) Assignee: DSM IP ASSETS B.V., Heerlen (NL)

( * ) Notice: Subject to any disclaimer, the term of this patent is extended or adjusted under 35 U.S.C. 154(b) by 57 days.

(21) Appl. No.: 14/647,332

(22) PCT Filed: Nov. 27, 2013

(86) PCT No.: PCT/EP2013/074885
§ 371 (c)(1),
(2) Date: May 26, 2015

(87) PCT Pub. No.: WO2014/083067
PCT Pub. Date: Jun. 5, 2014

(65) Prior Publication Data
US 2015/0320683 A1    Nov. 12, 2015

(30) Foreign Application Priority Data

Nov. 27, 2012    (EP) .................................... 12194399

(51) Int. Cl.
| | | |
|---|---|---|
| *A61K 9/16* | (2006.01) | |
| *A61K 8/31* | (2006.01) | |
| *A61K 31/015* | (2006.01) | |
| *A61K 8/73* | (2006.01) | |
| *A61Q 19/00* | (2006.01) | |
| *A61K 8/02* | (2006.01) | |
| *B01J 2/20* | (2006.01) | |
| *A23K 20/174* | (2016.01) | |
| *A23P 30/20* | (2016.01) | |
| *A23L 5/44* | (2016.01) | |
| *A23L 33/105* | (2016.01) | |
| *A23L 33/155* | (2016.01) | |

(52) U.S. Cl.
CPC .......... *A61K 9/1694* (2013.01); *A23K 20/174* (2016.05); *A23L 5/44* (2016.08); *A23L 33/105* (2016.08); *A23L 33/155* (2016.08); *A23P 30/20* (2016.08); *A61K 8/0241* (2013.01); *A61K 8/31* (2013.01); *A61K 8/732* (2013.01); *A61K 9/1652* (2013.01); *A61K 31/015* (2013.01); *A61Q 19/00* (2013.01); *B01J 2/20* (2013.01); *A23V 2002/00* (2013.01); *A61K 2800/10* (2013.01); *A61K 2800/412* (2013.01); *A61K 2800/413* (2013.01); *A61K 2800/652* (2013.01)

(58) Field of Classification Search
CPC ................................... A61K 9/16; A61K 8/31
See application file for complete search history.

(56) References Cited

U.S. PATENT DOCUMENTS

2008/0181960 A1\* 7/2008 Doney .................. A61K 9/146
424/489

FOREIGN PATENT DOCUMENTS

| WO | WO 01/25414 | 4/2001 |
|---|---|---|
| WO | WO 01/62226 | 8/2001 |
| WO | WO 2010/040683 | 4/2010 |
| WO | WO 2013/127807 | 9/2013 |

OTHER PUBLICATIONS

International Search Report for PCT/EP2013/074885 dated Feb. 10, 2014, 4 pages.
Bhaskaran et al., "Extrusion Spheronization—A Review", *International Journal of PharmTech Research CODEN (USA)*, Oct. 1, 2010, vol. 2, No. 4, pp. 2429-2433.

\* cited by examiner

*Primary Examiner* — Benjamin Packard
(74) *Attorney, Agent, or Firm* — Nixon & Vanderhye P.C.

(57) ABSTRACT

The present invention relates to a process for the production of discrete solid extruded particles comprising dispersion droplets, to such particles as well as to the use of such particles in food, feed, pharmaceutical and personal care applications.

16 Claims, No Drawings

PROCESS FOR THE PRODUCTION OF DISCRETE SOLID EXTRUDED PARTICLES

This application is the U.S. national phase of International Application No. PCT/EP2013/074885 filed 27 Nov. 2013, which designated the U.S. and claims priority to EP Patent Application No. 12194399.7 filed 27 Nov. 2012, the entire contents of each of which are hereby incorporated by reference.

The present invention relates to a process for the production of discrete solid extruded particles comprising dispersion droplets, to such particles as well as to the use of such particles in food, feed, pharmaceutical and personal care applications.

The dispersions which are extruded are solid lipophilic active-in-water-dispersions comprising at least one carotenoid and at least one emulsifying protective colloid and water.

The terms "emulsion" and "dispersion" in the context of the present invention are synonyms. A dispersion in the context of the present invention comprises (at least). one (or more) carotenoid and one (or more) emulsifier and water.

There are many ways to formulate carotenoids. The types of formulations are depending i.e. on the use of these formulations in the final application as well as on the kind of material (ingredients) which are used. However, the most important and demanding formulations are the so-called dried dispersions. The carotenoid is emulsified into an aqueous phase containing a matrix material and/or a suitable emulsifying protective colloid. After drying, the carotenoid is embedded in the matrix material. It is possible that the carotenoid is (partially) crystallised in the extrudate.

Known technologies for dispersions are e.g. rotor-stator-systems, high pressure homogenizers or ultrasonic devices. A major disadvantage of these technologies is that a relatively low viscosity (usually below 1 Pas) is required, leading to high amounts of water in the dispersion. Usually these processes require the use of an organic solvent which has to be removed after dispersion or precipitation.

Extrusion processes (and extruders) are well known in the field of formulations. They can be used for many different kinds of materials. They can be used for many different kinds of materials, such as thermoplastics and rubbers, as well as food- and feedstuffs.

The main advantages of using the extrusion technology is that high viscous solutions can be formulated and less water can be used for the dispersion, which then requires less drying. Furthermore an extrusion process can be run as a continuous process and it can be run without organic solvents.

It can be found in the prior art that emulsions comprising fat soluble vitamins are extruded. U.S. 2004/0201116 discloses pellets which are obtained by a combination of producing emulsions using devices like high pressure homogenizers with subsequent direct pelleting or extrusion as a second process step.

The goal of the present invention was to find a way to improve (also simplify) the production of extrudates comprising solid lipophilic active-in-water-dispersion droplets comprising at least one carotenoid and at least one emulsifying protective colloid and water.

These extrudates should then also be formed into a good flowable form which has a low fraction of the solid lipophilic active-in-water-dispersion droplets on the particle surface.

Carotenoids are distinctly different from lipophilic vitamins and lipophilic flavours. These lipophilic vitamins are either liquid or can easily be made liquid by using reasonable temperatures well below 100° C. Carotenoids are lipophilic, cannot be melted around 100° C., and decompose at higher temperatures. They are classical representative of the so-called sparingly soluble lipophilic actives.

A new way for the production of such discrete solid particles was found. Surprisingly it was found out that when the dispersion process is carried out inside the extruder, and then afterward the extrudates are further formed into discrete solid particles, the process as well as the obtained extrudates and discrete solid particles are improved.

When the dispersion process is carried out in the extruder (extrudation apparatus), and wherein afterward the extrudates are further formed into discrete solid extruded particles, (i) very small average dispersion droplets sizes can be obtained, and
(ii) a very narrow and monomodal distribution of the droplet sizes is obtained, and
(iii) such a process can easily be run as a continuous process, and
(iv) no organic solvent is used and
(v) less water can be used and therefore less energy for drying the extrudate is necessary, and
(vi) good flowablity of the discrete solid extruded particles.

Therefore the present invention relates to a process of production of discrete solid extruded particles, wherein an extrudate comprising solid lipophilic active-in-water-dispersion ingredient droplets, wherein said dispersion comprises at least one carotenoid and at least one emulsifying protective colloid and water, is produced by extrusion in a first step, and after the extrusion the extrudate is further formed into discrete solid extruded particles.

A preferred embodiment of the present invention relates to a process as described above, wherein the solid lipophilic active-in-water-dispersion droplets comprising at least one carotenoid (as solid lipophilic active) and at least one emulsifying protective colloid and water, and wherein the emulsifying process is carried out in the extruder.

A preferred embodiment of the present invention relates to a process as described above wherein the extrudate is further formed into discrete solid extruded particles by cutting and drying.

A preferred embodiment of the present invention relates to a process as described above wherein the drying can be carried out before cutting, during the cutting or after the cutting, as well as a combination thereof (=any sequence of drying and cutting).

A preferred embodiment of the present invention relates to a process as described above wherein the extrudate is further formed into discrete solid extruded particles by a spheronisation process.

The term "carotenoid" as used herein comprises a natural or synthetic carotene or structurally related polyene compound which can be used as a functional health ingredient or colorant for food, such as α- or β-carotene, 8'-apo-β-carotenal, 8'-apo-β-carotenoic acid esters such as the ethyl ester, canthaxanthin, astaxanthin, lycopene, lutein, zeaxanthin or crocetin, or mixtures thereof. The preferred carotenoids are β-carotene, lycopene and lutein and mixtures thereof, especially β-carotene.

Therefore a preferred embodiment of the present invention is a process as described above, wherein the one or more carotenoid is chosen from the group consisting of α-carotene, β-carotene, 8'-apo-β-carotenal, 8'-apo-β-carotenoic acid esters such as the ethyl ester, canthaxanthin, astaxanthin, lycopene, lutein, zeaxanthin and crocetin.

In an especially preferred process the carotenoid is β-carotene.

At least one emulsifying protective colloid is used in the process according to the present invention. The term emulsifying protective colloid cover all protective colloids having emulsifying properties. Any commonly known and used emulsifying protective colloid can be used. The emulsifying protective colloid can be chosen depending on the final use of the extrudate afterwards. That means if the extrudate obtained by the process according to the present invention is used in food or feed product, the emulsifying protective colloid must be food or feed grade. And in case it is used in pharmaceutical application the emulsifier must be pharma grade.

Suitable emulsifying protective colloids are i.e. modified (food) starches, ascorbyl palmitate, pectin, alginate, carrageenan, furcellaran, dextrin derivatives, celluloses and cellulose derivatives (e.g. cellulose acetate, methyl cellulose, hydroxypropyl methyl cellulose), lignosulfonate, polysaccharide gums (such as gum acacia (=gum arabic), flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof).

The starches can be modified physically and chemically. Pregelatinized starches are examples of physically modified starches. Acidic modified, oxidized, cross-linked, starch esters, starch ethers and cationic starches are examples of chemically modified starches.

A preferred embodiment therefore relates to process, wherein at least one emulsifying protective colloid is chosen from the group consisting of modified (food) starches, ascorbyl palmitate, pectin, alginate, carrageenan, furcellaran, dextrin derivatives, celluloses and cellulose derivatives (e.g. cellulose acetate, methyl cellulose, hydroxypropyl methyl cellulose), lignosulfonate, polysaccharide gums (such as gum acacia (=gum arabic), flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof).

Water is also used in the process according to the present invention. But as mentioned before, it is possible to run the process with less water when compared to the usually used processes.

No organic solvent is used in the process according to the present invention.

It is also possible to add further ingredients (auxiliary agents) during the process of formulation (extrudation).

Such auxiliary agents can be useful for the extrusion process
and/or for the extrudate,
and/or for the discrete solid particles,
and/or for the product (or application), wherein the discrete solid particles are used afterwards.

Such auxiliary agents are for example
antioxidants (such as ascorbic acid or salts thereof, tocopherol (synthetic or natural)), butylated hydroxytoluene (BHT), ascorbyl palmitate, butylated hydroxyanisole (BHA), propyl gallate, tert. butyl hydroxyquinoline, ethoxyquin and/or ascorbic acid esters of a fatty acid);
plasticisers (such as fructose, glucose, glycerol, mannitol, invert sugar syrup, sorbitol, sucrose, xylitol, propylene glycol, ester of citric acid, lactitol, erythritol and maltitol);
stabilisers (such as gel-forming agents as xanthan gum, gellan gum);
humectants (such as glycerine, sorbitol, polyethylene glycol);
dyes;
fragrances;
fillers and
buffers.

These auxiliary agents are added optionally. When added then the amount of the auxiliary agents goes from 1 to 85 weight-% (wt.-%), based on the total weight of the dispersion.

All the preferences listed above for the carotenoids, the emulsifying protective colloids and the auxiliary agents also apply to the composition of the extrudates as well as to the discrete solid extruded particles.

In a preferred process according to the present invention 0.5 wt.-% to 50 wt.-%, preferably 1 wt.-% to 45 wt.-%, more preferably 1 wt.-% to 30 wt.-%, even more preferably 1 wt.-% to 20 wt.-%, especially preferably 1 wt.-% to 15 wt.-%, based on the total weight of the dispersion, of at least one carotenoid are used.

In a preferred process according to the present invention 5 wt.-% to 80 wt.-%, more preferably 8 wt.-% to 80 wt.-%, even more preferably 10 wt.-% to 80 wt.-%, based on the total weight of the dispersion, of at least one emulsifying protective colloid are used.

In a preferred process according to the present invention 1 wt.-% to 90 wt.-%, more preferably 1 wt.-% to 80 wt.-%, based on the total weight of the dispersion, of water are used.

In a preferred process according to the present invention 1 wt.-% to 85 wt.-%, based on the total weight of the dispersion, of at least one auxiliary agent are used.

Therefore a preferred embodiment of the present invention relates a process of production of discrete solid extruded particles, wherein an extrudate comprising solid lipophilic active-in-water-dispersion droplets is produced by extrusion in a first step, wherein said dispersion comprises
0.5 wt.-% to 50 wt.-%, based on the total weight of the dispersion, of at least one carotenoid, and
5 wt.-% to 80 wt.-%, based on the total weight of the dispersion, of at least one emulsifying protective colloid, and
1 wt.-% to 90 wt.-%, based on the total weight of the dispersion, of water and
1 wt.-% to 85 wt.-%, based on the total weight of the dispersion, of at least one auxiliary agent, and
wherein after the extrusion the extrudate is further formed into discrete solid extruded particles.

Therefore a preferred embodiment of the present invention relates to a process of production of discrete solid extruded particles, wherein an extrudate comprising solid lipophilic active-in-water-dispersion droplets is produced by extrusion in a first step,
wherein said dispersion comprises
1 wt.-% to 45 wt.-%, based on the total weight of the dispersion, of at least one carotenoid chosen from the group consisting of α-carotene, β-carotene, 8'-apo-β-carotenal, 8'-apo-β-carotenoic acid esters such as the ethyl ester, canthaxanthin, astaxanthin, lycopene, lutein, zeaxanthin and crocetin, and 8 wt.-% to 80 wt.-%, based on the total weight of the dispersion, of at least one emulsifying protective colloid chosen from the group consisting of modified (food) starches, ascorbyl palmitate, pectin, alginate, carrageenan, furcellaran, dextrin derivatives, celluloses and cellulose derivatives (e.g. cellulose acetate, methyl cellulose, hydroxypropyl methyl cellulose), lignosulfonate, polysaccharide gums (such as gum acacia (=gum arabic), flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof), and 1 wt.-% to 80 wt.-%, based on the total weight of the dispersion, of water and 1 wt.-% to 80 wt.-%, based on the total weight of the dispersion, of at least one auxiliary agent chosen from the group consisting of antioxidants (such as ascorbic acid or salts thereof, tocopherol (synthetic or natural); butylated hydroxytoluene (BHT); butylated hydroxyanisole (BHA); ascorbyl palmitate; propyl gallate; tert. butyl hydroxyquinoline, ethoxyquin, and/or ascorbic acid esters of a fatty acid); plasticisers (such as fructose, glucose, glycerol, mannitol, invert sugar syrup, sorbitol, sucrose, xylitol, propylene glycol, ester of citric acid, lactitol, erythritol and maltitol); stabilisers (such as gel-forming agents as xanthan gum, gellan gum); humectants (such as glycerine, sorbitol, polyethylene glycol); dyes; fragrances; fillers and buffers, and wherein after the extrusion the extrudate is further formed into discrete solid extruded particles.

Therefore a more preferred embodiment of the present invention relates to a process of production of discrete solid extruded particles, wherein an extrudate comprising solid lipophilic active-in-water-dispersion droplets is produced by extrusion in a first step, wherein the dispersion comprises 1 wt.-% to 30 wt.-%, preferably 1 wt.-% to 20 wt.-%, more preferably 1 wt.-% to 15 wt.-%, based on the total weight of the dispersion, of β-carotene, and 10 wt.-% to 80 wt.-%, based on the total weight of the dispersion, of at least one (modified) food starch, and 1 to 60 wt.-%, based on the total weight of the dispersion, of water and 1 to 80 wt.-%, based on the total weight of the dispersion, of at least one auxiliary agent chosen from the group consisting of antioxidants (such as ascorbic acid or salts thereof, tocopherol (synthetic or natural); butylated hydroxytoluene (BHT); butylated hydroxyanisole (BHA); ascorbyl palmitate; propyl gallate; tert. butyl hydroxyquinoline, ethoxyquin, and/or ascorbic acid esters of a fatty acid); plasticisers (such as fructose, glucose, glycerol, mannitol, invert sugar syrup, sorbitol, sucrose, xylitol, propylene glycol, ester of citric acid, lactitol, erythritol and maltitol); stabilisers(such as gel-forming agents as xanthan gum, gellan gum); humectants (such as glycerine, sorbitol, polyethylene glycol); dyes; fragrances; fillers and buffers, and wherein after the extrusion the extrudate is further formed into discrete solid extruded particles.

One of the advantages of the present invention is that the size distribution of the average droplet sizes of the solid lipophilic active-in-water-dispersion inside the extrudate (and in the discrete solid extruded particles) is narrow and monomodal. This means that the carotenoid is nearly homogenously distributed inside the extrudate (and in the discrete solid extruded particles), which allows afterwards very precise dosages.

Furthermore, the process according to the present invention allows to producing very small sized droplets of the solid lipophilic active-in-water-dispersion inside the extrudate (and in the discrete solid extruded particles). The average droplet size can be as small as 50 nm. Usually the droplets are smaller than 1 µm.

Preferably the average droplet size ($d_{3,2}$) of the solid lipophilic active-in-water-dispersion the extrudate (and in the discrete solid extruded particles) is between 50 nm and 300 nm.

The droplet sizes are measured by using commonly known and standardized methods. Suitable methods are light scattering or laser diffraction.

More preferably the average droplet size ($d_{3,2}$) of the solid lipophilic active-in-water-dispersion inside the extrudate (and in the discrete solid extruded particles) is between 100 nm and 200 nm.

The extrusion process is characterised in that the dispersion process is carried out inside the extruder. Usually the three main ingredients (carotenoid and emulsifying protective colloid and water) are added at different inlets of the extruder process. These inlets are arranged separated from each other. When (optionally) auxiliary agents are added, they can be added together with one or more of the main ingredients or they can also be added in a separate step.

Usually the emulsifying protective colloid is added first, then the water and then the carotenoid is added. It is also possible that one ingredient is added through more than one inlet of the extruder at different locations. Therefore a further embodiment of the present invention relates to a process, wherein the emulsifying protective colloid (or a mixture of emulsifiers) is added first, then the water and then afterwards the carotenoid (or a mixture of carotenoids).

A preferred embodiment of the present invention relates to a process wherein the carotenoid is β-carotene. In this case β-carotene is either added (i) as a liquid (molten) into the extruder (optionally premixed with an oil), or (ii) as a solid powder (optionally premixed with at least one modified (food) starch and wherein the powder can be added to the process at the start of the extruder or at any stage)

The temperature inside the extruder is usually between 20 and 220° C. Preferably the temperature of extrudate exiting the extruder is <100° C. The total residence time for the ingredients in the extruder is usually between 1 and 400 s.

The amount of shear of the extrusion process according to the present invention is usually 200 to 80000 units.

Furthermore, it is also possible to pump inert gas through the extruder. The inert gas is usually pumped in at the entrance of the extruder. But it could also be pumped in at any stage of the extrusion process (also through several inlets at different locations). Inert gas can be helpful to protect sensible ingredients.

The extruder comprises usually one or more screw shafts on which various conveying or kneading type screw elements are mounted.

The material is transported by these elements through the extruder (optionally under pressure and elevated temperature). At the end (exit) of the extruder there can be a die through which the extruded material is pressed. Afterwards the extruded material is dried and cut (or also vice versa). The extruder can have several inlets through which the material can be added.

In the case of the present invention there are several inlets to add the emulsifier(s), the carotenoid(s), water and optionally the auxiliary agents.

An essential feature of the present invention is that the extrudate is (after the extrusion process) further formed into discrete solid extruded particles.

This forming step can be carried out by using various processes.

It is suitable to carry out this forming step by cutting and drying the extrudate. The drying can be carried out before cutting, during the cutting or after the cutting, as well as any other combination thereof.

The cutting can be carried out by any known device used in the extruder technology. The cutting conditions are related to the desired size of the discrete solid extruded particles.

The drying can be carried out by any known device. The drying conditions are related to the desired size and desired final water content of the discrete solid extruded particles.

It is also suitable to carry out this forming step by a spheronisation process. The spheronisation process ("spheronisation") is a known process. During spheronisation cylindrical extrudate strands are converted into spherical, solid particles. In this process, the extrudate strands are broken down into segments and then rounded until they have the desired shape. Finally they are discharged from the spheroniser and transferred to an optional drying step to obtain the final water content in the pellets.

The present invention also relates to discrete solid extruded particles obtainable by a process (as described above), wherein the discrete solid extruded particles comprise solid lipophilic active-in-water-dispersion droplets, wherein these dispersion droplets comprise at least one carotenoid and at least one emulsifying protective colloid and water, characterised in that after the extrusion the extrudate is further formed into the discrete solid extruded particles.

Preferably, the present invention also relates to discrete solid extruded particles obtainable by a process (as described above), wherein the discrete solid extruded particles comprise solid lipophilic active-in-water-dispersion droplets, wherein these dispersion droplets comprise at least one carotenoid and at least one emulsifying protective colloid and water, characterised in that after the extrusion the extrudate is further formed into the discrete solid extruded particles, and wherein the dispersion process is carried out in the extruder.

All the preferences as described above also apply for such discrete solid extruded particles obtainable by the inventive process.

A further embodiment of the present invention relates to new discrete solid extruded particles. These inventive discrete solid extruded particles comprise solid lipophilic active-in-water-dispersion droplets which have a very small average droplet size, and wherein the distribution of the droplet sizes is narrow and (almost) monomodal.

The particle sizes of the discrete solid extruded particles are lower than 1000 μm. preferably lower than 700 μm. Usually between 50-700 μm.

It is also possible to produce discrete solid extruded particles having a particle size between 50-500 μm or having a particle size between 100-400 μm.

The particle size distribution of the discrete solid extruded particles is quite narrow. The shape of the discrete solid extruded particles is preferably spherical.

The particle size and shape are determined by using well known methods, such as optical microscopy, (scanning) electron microscopy or laser diffraction (only for size). The particle size in the context of the present invention is defined as the longest dimension of a particle (such i.e. the diameter in case of spherical particle or in case of non-spherical particles the diameter of an equivalent sphere).

Therefore a further embodiment of the present invention relates to discrete solid extruded particles comprising solid lipophilic active-in-water-dispersion droplets, wherein these dispersion droplets comprise
at least one carotenoid and
at least one emulsifying protective colloid, and
water, and optionally
at least one auxiliary agent,
characterised in that the average particle size of the solid lipophilic active-in-water-dispersion droplets inside the discrete solid extruded particles are less than 300 nm (preferably the average particle size of the solid lipophilic active-in-water-dispersion droplets is between 100 nm and 200 nm), characterised that the discrete solid extruded particles comprise less than 10 wt-%, based on the total weight of the discrete solid extruded particles, of water (preferably less than 6 wt-%).

The average particle sizes of the solid lipophilic active-in-water-dispersion droplets are measured by laser diffraction, e.g. with a Malvern Mastersizer 2000 and Hydro 2000 S sample dispersion unit. The average particle size of the solid lipophilic active-in-water-dispersion droplets can also be determined by dynamic light scattering, e.g. with a Malvern Zetasizer Nano.

Preferred discrete solid extruded particles according to the present invention comprise:
0.5 wt.-% to 50 wt.-%, based on the total weight of the discrete solid extruded particles, of at least one carotenoid, and
5 wt.-% to 80 wt.-%, based on the total weight of the discrete solid extruded particles, of at least one emulsifying protective colloid, and
less than 10 wt.-%, based on the total weight of the discrete solid extruded particles, of water and optionally
1 wt.-% to 85 wt.-%, based on the total weight of the discrete solid extruded particles, of at least one auxiliary agent,
characterised in that the average particle sizes of the solid lipophilic active-in-water-dispersion droplets inside the discrete solid extruded particles are less than 300 nm (preferably the average particle sizes of the solid lipophilic active-in-water-dispersion droplets are between 100 nm and 200 nm).

The particle sizes of these discrete solid extruded particles are lower than 1000 μm. preferably lower than 700 μm. Usually between 50-700 μm.

More preferred are discrete solid extruded particles comprising
1 wt.-% to 45 wt.-%, based on the total weight of the discrete solid extruded particles, of at least one carotenoid chosen from the group consisting of α-carotene, β-carotene, 8'-apo-β-carotenal, 8'-apo-β-carotenoic acid esters such as the ethyl ester, canthaxanthin, astaxanthin, lycopene, lutein, zeaxanthin and crocetin, and
8 wt.-% to 80 wt.-%, based on the total weight of the discrete solid extruded particles, of at least one emulsifying protective colloid chosen from the group consisting of modified (food) starches, ascorbyl palmitate, pectin, alginate, carrageenan, furcellaran, dextrin derivatives, celluloses and cellulose derivatives (e.g. cellulose acetate, methyl cellulose, hydroxypropyl methyl cellulose), lignosulfonate, polysaccharide gums (such as gum acacia (=gum arabic), flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof), and less than 6 wt.-%, based on the total weight of the discrete solid extruded particles, of water, and 1 wt.-% to 80 wt.-%, based on the total weight of the discrete solid extruded particles, of at least one auxiliary agent, wherein the auxiliary agent is chosen from the group consisting of antioxidants (such as ascorbic acid or salts thereof, tocopherol (synthetic or natural)), butylated hydroxytoluene (BHT), ascorbyl palmitatebutylated hydroxyanisole (BHA), propyl gallate, tert. butyl hydroxyquinoline, ethoxyquin and/or ascorbic acid esters of a fatty acid); plasticisers (such as fructose, glucose, glycerol, mannitol, invert sugar syrup, sorbitol, sucrose, xylitol, propylene glycol, ester of citric acid, lactitol, erythritol and maltitol); stabilisers (such as gel-forming agents as xanthan gum, gellan gum); humectants (such as glycerine, sorbitol, polyethylene glycol); dyes; fragrances; fillers and buffers, characterised in that the average particle size of the solid lipophilic active-in-water-dispersion droplets inside the discrete solid extruded particles is less than 300 nm (preferably the average particle size of the solid lipophilic active-in-water-dispersion droplets is between 100 nm and 200 nm) and wherein the particle sizes of the discrete solid extruded particles are lower than 1000 μm (preferably lower than 700 μm, more preferably between 50-700 μm).

Further more preferred are discrete solid extruded particles comprising 1 wt.-% to 30 wt.-%, based on the total weight of the discrete solid extruded particles, of at least one carotenoid chosen from the group consisting of α-carotene, β-carotene, 8'-apo-β-carotenal, 8'-apo-β-carotenoic acid esters such as the ethyl ester, canthaxanthin, astaxanthin, lycopene, lutein, zeaxanthin and crocetin, and 10 wt.-% to 80 wt.-%, based on the total weight of the discrete solid extruded particles, of at least one emulsifying protective colloid chosen from the group consisting of modified (food) starches, ascorbyl palmitate, pectin, alginate, carrageenan, furcellaran, dextrin derivatives, celluloses and cellulose derivatives (e.g. cellulose acetate, methyl cellulose, hydroxypropyl methyl cellulose), lignosulfonate, polysaccharide gums (such as gum acacia (=gum arabic), flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof), and less than 6 wt.-%, based on the total weight of the discrete solid extruded particles, of water, and 1 wt.-% to 80 wt.-%, based on the total weight of the discrete solid extruded particles, of at least one auxiliary agent, wherein the auxiliary agent is chosen from the group consisting of antioxidants (such as ascorbic acid or salts thereof, tocopherol (synthetic or natural)), butylated hydroxytoluene (BHT), ascorbyl palmitatebutylated hydroxyanisole (BHA), propyl gallate, tert. butyl hydroxyquinoline, ethoxyquin and/or ascorbic acid esters of a fatty acid); plasticisers (such as fructose, glucose, glycerol, mannitol, invert sugar syrup, sorbitol, sucrose, xylitol, propylene glycol, ester of citric acid, lactitol, erythritol and maltitol); stabilisers (such as gel-forming agents as xanthan gum, gellan gum); humectants (such as glycerine, sorbitol, polyethylene glycol); dyes; fragrances; fillers and buffers, characterised in that the average particle size of the solid lipophilic active-in-water-dispersion droplets inside the discrete solid extruded particles is less than 300 nm (preferably the average particle size of the solid lipophilic active-in-water-dispersion droplets is between 100 nm and 200 nm) and wherein the particle sizes of the discrete solid extruded particles are lower than 1000 μm (preferably lower than 700 μm, more preferably between 50-700 μm).

Most preferred are discrete solid extruded particles comprising 1 wt.-% to 20 wt.-%, preferably 1 wt.%-15 wt.-%, based on the total weight of the discrete solid extruded particles, of β-carotene, and 10 wt.-% to 80 wt.-%, based on the total weight of the discrete solid extruded particles, of at least one modified (food) starch, and less than 6 wt.-%, based on the total weight of the discrete solid extruded particles, of water, and 1 wt.-% to 80 wt.-%, based on the total weight of the discrete solid extruded particles, of at least one auxiliary agent, wherein the auxiliary agent is chosen from the group consisting of antioxidants (such as ascorbic acid or salts thereof, tocopherol (synthetic or natural)), butylated hydroxytoluene (BHT), ascorbyl palmitatebutylated hydroxyanisole (BHA), propyl gallate, tert. butyl hydroxyquinoline, ethoxyquin and/or ascorbic acid esters of a fatty acid); plasticisers (such as fructose, glucose, glycerol, mannitol, invert sugar syrup, sorbitol, sucrose, xylitol, propylene glycol, ester of citric acid, lactitol, erythritol and maltitol); stabilisers (such as gel-forming agents as xanthan gum, gellan gum); humectants (such as glycerine, sorbitol, polyethylene glycol); dyes; fragrances; fillers and buffers, characterised in that the average particle size of the solid lipophilic active-in-water-dispersion droplets inside the discrete solid extruded particles is less than 300 nm (preferably the average particle size of the solid lipophilic active-in-water-dispersion droplets is between 100 nm and 200 nm) and wherein the particle sizes of the discrete solid extruded particles are lower than 1000 μm (preferably lower than 700 μm, more preferably between 50-700 μm).

The discrete solid extruded particles as obtained by the process as described above can be used in many fields of applications. Preferably the discrete solid extruded particles as disclosed and described above are used in food, feed, pharmaceutical and personal care products.

Therefore a further embodiment of the present invention relates to the use of the discrete solid extruded particles as disclosed and described above in food, feed, pharmaceutical and/or personal care products. It is to be mentioned that dietary supplements are part of our definition of food products.

A further embodiment of the present invention relates to food, feed, pharmaceutical or personal care products comprising discrete solid extruded particles as disclosed and described above.

The so obtained products do have good storage stabilities.

The following Example serves to illustrate the invention. All percentages and parts (if not otherwise indicated) are related to the weight. The temperature is given (if not otherwise indicated) in degree Celsius.

EXAMPLE

Example 1

Dispersion of β-Carotene in Modified Food Starch

The extrusion dispersion of β-carotene in 10.5 g modified food starch is conducted on a laboratory-scale conical twin-screw (batch) extruder (DSM Xplore 15 ml micro-compounder). 10.5 g of modified food starch (HICAP 100, National Starch), is mixed with 0.75 g of β-carotene (DSM Nutritional Products) and 3.75 g demineralized water. The extruder is operated at a screw speed of 120 rpm and a barrel temperature of 200° C. The feed hopper and extruder are purged with nitrogen. The mixture is placed in the feed hopper, allowed to pass once through the extruder and exit through a 1 mm die.

The obtained extrudate strand is partly soluble in water resulting in an orange, cloudy solution stable over 12 hours. This solution is filtered either with a folded filter paper (grade 597½: 5-7 μm) or a syringe driven filter unit (0.22 μm). Filtration with the larger pores resulted in a turbid, light-yellow solution, while the solution from the fine filter was clear. The hydrodynamic droplet size in these solutions is measured by dynamic light scattering (Malvern Zetasizer). The average droplet size (Z-Average) in the clear solution is 184 nm, while the turbid solution also contains some larger droplets/particles resulting in a Z-Average of 625 nm. The extrudate strand containing the dispersed β-carotene is let to cool down to room temperature. Subsequently the strands are cut into discrete, solid particles with a pelletizer (Thermo Fisher Scientific) and finally dried in a laboratory-scale fluid bed drier (Retsch TG 200) to obtain a final water content of 6 wt %.

The invention claimed is:

1. A process for production of discrete solid extruded particles comprising solid carotenoid-in-water dispersion droplets, wherein the process comprises:
   (i) emulsifying ingredients comprised of at least one carotenoid, at least one emulsifying protective colloid and water in an extruder to form solid carotenoid-in-water dispersion droplets,
   (ii) extruding extrudate strands which comprise the solid carotenoid-in-water dispersion droplets from the extruder, and
   (iii) forming discrete solid extruded particles from the extrudate strands.

2. The process according to claim 1, wherein step (iii) includes forming the extrudate strands into discrete solid extruded particles by cutting and drying.

3. The process according to claim 2, wherein the drying is practiced in any sequence of before, during and/or after cutting of the extrudate strand.

4. The process according to claim 1, wherein step (iii) further comprises subjecting the discrete solid extruded particles to a spheronisation process to thereby form substantially spherical discrete solid particles therefrom.

5. The process according to claim 1, wherein the carotenoid is at least one selected from the group consisting of α-carotene, β-carotene, 8'-apo-β-carotenal, 8'-apo-β-carotenoic acid esters, canthaxanthin, astaxanthin, lycopene, lutein, zeaxanthin and crocetin.

6. The process according to claim 1, wherein the carotenoid is β-carotene.

7. The process according to claim 1, wherein the emulsifying protective colloid is at least one selected from the group consisting of modified food starches, ascorbyl palmitate, pectin, alginate, carrageenan, furcellaran, dextrin derivatives, celluloses and cellulose derivatives, lignosulfonate, polysaccharide gums, bovine gelatine, fish gelatine, pork gelatine, poultry gelatine, plant proteins, animal proteins, milk whey proteins, lecithin, polyglycerol esters of fatty acids, monoglycerides of fatty acids, diglycerides of fatty acids, sorbitan ester, PG esters, sugar esters and derivatives thereof.

8. The process according to claim 1, wherein the at least one carotenoid is present in step (i) in an amount of 0.5 wt.-% to 50 wt.-%, based on the total weight of the dispersion.

9. The process according to claim 1, wherein the at least one emulsifying protective colloid is present in step (i) in an amount of 5 wt.-% to 80 wt.-%, based on the total weight of the dispersion.

10. The process according to claim 1, wherein the water is present in step (i) in an amount of 1 wt.-% to 90 wt.-%, based on the total weight of the dispersion.

11. The process according to claim 10, wherein the water is present in step (i) in an amount of 1 wt.-% to 80 wt.-%, based on the total weight of the dispersion.

12. The process according to claim 1, wherein the ingredients emulsified according to step (i) further comprise 1 wt.-% to 85 wt.-%, based on the total weight of the dispersion, of at least one auxiliary agent.

13. The process according to claim 12, wherein the auxiliary agent is at least one selected from the group consisting of antioxidants, plasticisers, stabilisers, humectants, dyes, fragrances, fillers and buffers.

14. The process according to claim 1, wherein step (i) comprises sequentially adding to the extruder the emulsifying protective colloid, followed by the water and then the at least one carotenoid.

15. The process according to claim 1, which comprises operating the extruder such that a temperature inside the extruder is between 20° C. and 220° C.

16. The process according to claim 1, wherein the total residence time in the extruder for the ingredients is between 1 and 400 s.

* * * * *